US007897801B2

(12) United States Patent
Rosier et al.

(10) Patent No.: US 7,897,801 B2
(45) Date of Patent: Mar. 1, 2011

(54) PROCESS FOR THE PREPARATION OF DINITRILES

(75) Inventors: Cécile Rosier, Soucieu en Jarrest (FR); Philippe Leconte, Meyzieu (FR); Damien Bourgeois, Lyons (FR)

(73) Assignee: Invista North America S.A R.L., Wilmington, DE (US)

( * ) Notice: Subject to any disclaimer, the term of this patent is extended or adjusted under 35 U.S.C. 154(b) by 620 days.

(21) Appl. No.: 10/556,629

(22) PCT Filed: May 7, 2004

(86) PCT No.: PCT/FR2004/001108
§ 371 (c)(1),
(2), (4) Date: Feb. 12, 2007

(87) PCT Pub. No.: WO2004/101497
PCT Pub. Date: Nov. 25, 2004

(65) Prior Publication Data
US 2007/0260086 A1   Nov. 8, 2007

(30) Foreign Application Priority Data
May 12, 2003   (FR) .................................... 03 05672

(51) Int. Cl.
*C07C 253/08* (2006.01)
(52) U.S. Cl. ........................................................ 558/334
(58) Field of Classification Search ................... 558/334
See application file for complete search history.

(56) References Cited

U.S. PATENT DOCUMENTS

| 2,402,873 | A | 6/1946 | Coffman et al. |
| 2,570,199 | A | 10/1951 | Brown |
| 2,583,984 | A | 1/1952 | Arthur, Jr. |
| 2,666,780 | A | 1/1954 | Arthur, Jr. |
| 2,768,132 | A | 10/1956 | Halliwell |
| 3,282,981 | A | 11/1966 | Davis |
| 3,297,742 | A | 1/1967 | Monroe, Jr. |
| 3,328,443 | A | 6/1967 | Clark |
| 3,340,207 | A | 9/1967 | Baker |
| 3,370,082 | A | 2/1968 | Eisfeld et al. |
| 3,496,210 | A | 2/1970 | Drinkard, Jr. |
| 3,496,215 | A | 2/1970 | Drinkard, Jr. |
| 3,496,217 | A | 2/1970 | Drinkard, Jr. |
| 3,496,218 | A | 2/1970 | Drinkard, Jr. |
| 3,522,288 | A | 7/1970 | Drinkard, Jr. |
| 3,526,654 | A | 9/1970 | Hildebrand |
| 3,536,748 | A | 10/1970 | Drinkard, Jr. |
| 3,538,142 | A | 11/1970 | Drinkard, Jr. |
| 3,542,847 | A | 11/1970 | Drinkard, Jr. |
| 3,547,972 | A | 12/1970 | Drinkard, Jr. |
| 3,551,474 | A | 12/1970 | Drinkard, Jr. |
| 3,563,698 | A | 2/1971 | Rushmere |
| 3,564,040 | A | 2/1971 | Downing |
| 3,579,560 | A | 5/1971 | Drinkard, Jr. |
| 3,631,191 | A | 12/1971 | Kane |
| 3,641,107 | A | 2/1972 | Breda |
| 3,651,146 | A | 3/1972 | Schriltz |
| 3,652,641 | A | 3/1972 | Druliner |
| 3,655,723 | A | 4/1972 | Drinkard, Jr. |
| 3,676,475 | A | 7/1972 | Drinkard, Jr. |
| 3,676,481 | A | 7/1972 | Chia |
| 3,694,485 | A | 9/1972 | Drinkard, Jr. |
| 3,739,011 | A | 6/1973 | Drinkard |
| 3,752,839 | A | 8/1973 | Drinkard |
| 3,766,231 | A | 10/1973 | Wayne |
| 3,766,237 | A | 10/1973 | Squire |
| 3,766,241 | A | 10/1973 | Drinkard |
| 3,773,809 | A | 11/1973 | Walter |
| 3,775,461 | A | 11/1973 | Drinkard |
| 3,798,256 | A | 3/1974 | King |
| 3,818,067 | A | 6/1974 | Downing |
| 3,818,068 | A | 6/1974 | Wells |
| 3,846,461 | A | 11/1974 | Shook |
| 3,846,474 | A | 11/1974 | Mok |
| 3,847,959 | A | 11/1974 | Shook |
| 3,849,472 | A | 11/1974 | Waddan |
| 3,850,973 | A | 11/1974 | Seidel |
| 3,852,325 | A | 12/1974 | King |
| 3,852,327 | A | 12/1974 | Druliner |
| 3,852,328 | A | 12/1974 | Chia |
| 3,852,329 | A | 12/1974 | Tomlinson |
| 3,853,754 | A | 12/1974 | Gosser |
| 3,853,948 | A | 12/1974 | Drinkard |
| 3,859,327 | A | 1/1975 | Wells |
| 3,864,380 | A | 2/1975 | King |
| 3,865,865 | A | 2/1975 | Musser |
| 3,869,501 | A | 3/1975 | Waddan |
| 3,884,997 | A | 5/1975 | Shook, Jr. |
| 3,903,120 | A | 9/1975 | Shook, Jr. |
| 3,920,721 | A | 11/1975 | Gosser |
| 3,925,445 | A | 12/1975 | King |
| 3,927,056 | A | 12/1975 | Gosser |
| 3,947,487 | A | 3/1976 | Crooks |
| 3,983,011 | A | 9/1976 | Wiggill |
| 3,997,579 | A | 12/1976 | Jesson |
| 4,045,495 | A | 8/1977 | Nazarenko |
| 4,046,815 | A | 9/1977 | Nazarenko |
| 4,076,756 | A | 2/1978 | Nazarenko |
| 4,080,374 | A | 3/1978 | Corn |
| 4,082,811 | A | 4/1978 | Shook, Jr. |
| 4,087,452 | A | 5/1978 | Kuntz |

(Continued)

FOREIGN PATENT DOCUMENTS

AU        6522096        2/1997

(Continued)

*Primary Examiner* — Joseph R Kosack
(74) *Attorney, Agent, or Firm* — Robert B. Furr, Jr.; Edward F. Kenehan, Jr.

(57) ABSTRACT

The present invention relates to a process for the preparation of dinitriles by hydrocyanation of unsaturated nitrile compounds in the presence of a catalyst based on a metal element in the zero oxidation state and on organophosphorus ligands; the invention relates more particularly to a process for the recovery from the hydrocyanation medium of a catalyst for the hydrocyanation of unsaturated nitrites to dinitriles. It consists in controlling the concentration of unsaturated nitrites in the reaction medium resulting from the hydrocyanation reaction in order to obtain a concentration by weight of unsaturated nitrites of less than 20% in the said medium, and in then feeding the said medium to a stage of settling into two upper and lower phases. The lower phase comprises most of the catalytic system, while the upper phase is composed essentially of the dinitriles.

26 Claims, No Drawings

U.S. PATENT DOCUMENTS

| | | |
|---|---|---|
| 4,134,923 A | 1/1979 | Reimer |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,230,634 A | 10/1980 | Benzie et al. |
| 4,240,976 A | 12/1980 | Benzie et al. |
| 4,251,468 A | 2/1981 | Nazarenko |
| 4,298,546 A | 11/1981 | Mc Gill |
| 4,328,172 A | 5/1982 | Rapoport |
| 4,330,483 A | 5/1982 | Rapoport |
| 4,336,110 A | 6/1982 | Reimer |
| 4,339,395 A | 7/1982 | Barnette |
| 4,347,193 A | 8/1982 | Shook, Jr. |
| 4,371,474 A | 2/1983 | Rapoport |
| 4,382,038 A | 5/1983 | Mc Gill |
| 4,385,007 A | 5/1983 | Shook, Jr. |
| 4,387,056 A | 6/1983 | Stowe |
| 4,394,321 A | 7/1983 | Cone |
| 4,416,824 A | 11/1983 | Reimer |
| 4,416,825 A | 11/1983 | Ostermaier |
| 4,434,316 A | 2/1984 | Barnette |
| 4,510,327 A | 4/1985 | Peet |
| 4,521,628 A | 6/1985 | Ostermaier |
| 4,539,302 A | 9/1985 | Leyendecker |
| 4,705,881 A | 11/1987 | Rapoport |
| 4,714,773 A | 12/1987 | Rapoport |
| 4,749,801 A | 6/1988 | Beatty |
| 4,774,353 A | 9/1988 | Hall |
| 4,783,546 A | 11/1988 | Burke |
| 4,810,815 A | 3/1989 | Bryndza |
| 4,874,884 A | 10/1989 | Mc Kinney |
| 4,990,645 A | 2/1991 | Back |
| 5,087,723 A | 2/1992 | Mc Kinney |
| 5,107,012 A | 4/1992 | Grunewald |
| 5,143,873 A | 9/1992 | Bryndza |
| 5,175,335 A | 12/1992 | Casalnuovo |
| 5,302,756 A | 4/1994 | McKinney |
| 5,312,957 A | 5/1994 | Casalnuovo |
| 5,312,959 A | 5/1994 | Sieja |
| 5,382,697 A | 1/1995 | Casalnuovo |
| 5,440,067 A | 8/1995 | Druliner |
| 5,449,807 A | 9/1995 | Druliner |
| 5,484,902 A | 1/1996 | Casalnuovo |
| 5,488,129 A | 1/1996 | Huser et al. |
| 5,510,470 A | 4/1996 | Casalnuovo |
| 5,512,695 A | 4/1996 | Kreutzer |
| 5,512,696 A | 4/1996 | Kreutzer |
| 5,523,453 A | 6/1996 | Breikss |
| 5,543,536 A | 8/1996 | Tam |
| 5,663,369 A | 9/1997 | Kreutzer |
| 5,688,986 A | 11/1997 | Tam |
| 5,693,843 A | 12/1997 | Breikss |
| 5,696,280 A | 12/1997 | Shapiro |
| 5,709,841 A | 1/1998 | Reimer |
| 5,723,641 A | 3/1998 | Tam |
| 5,773,637 A | 6/1998 | Cicha et al. |
| 5,821,378 A | 10/1998 | Foo |
| 5,847,191 A | 12/1998 | Bunel |
| 5,856,555 A | 1/1999 | Huser et al. |
| 5,908,805 A | 6/1999 | Huser et al. |
| 5,959,135 A | 9/1999 | Garner |
| 5,981,772 A | 11/1999 | Foo |
| 6,020,516 A | 2/2000 | Foo |
| 6,031,120 A | 2/2000 | Tam |
| 6,048,996 A | 4/2000 | Clarkson |
| 6,069,267 A | 5/2000 | Tam |
| 6,077,979 A | 6/2000 | Qiu |
| 6,090,987 A | 7/2000 | Billig et al. |
| 6,120,700 A | 9/2000 | Foo |
| 6,121,184 A | 9/2000 | Druliner |
| 6,127,567 A | 10/2000 | Garner |
| 6,147,247 A | 11/2000 | Voit et al. |
| 6,169,198 B1 | 1/2001 | Fischer et al. |
| 6,171,996 B1 | 1/2001 | Garner |
| 6,171,997 B1 | 1/2001 | Foo |
| 6,197,992 B1 | 3/2001 | Fischer et al. |
| 6,242,633 B1 | 6/2001 | Fischer et al. |
| 6,284,865 B1 | 9/2001 | Tam |
| 6,307,109 B1 | 10/2001 | Kanel et al. |
| 6,355,833 B2 | 3/2002 | Fischer et al. |
| 6,362,354 B1 | 3/2002 | Bunel |
| 6,372,147 B1 | 4/2002 | Reimer |
| 6,380,421 B1 | 4/2002 | Lu |
| 6,399,534 B2 | 6/2002 | Bunel |
| 6,420,611 B1 | 7/2002 | Tam |
| 6,461,481 B1 | 10/2002 | Barnette |
| 6,469,194 B2 | 10/2002 | Burattin et al. |
| 6,489,517 B1 | 12/2002 | Shapiro |
| 6,521,778 B1 | 2/2003 | Fischer et al. |
| 6,555,718 B1 | 4/2003 | Shapiro |
| 6,646,148 B1 | 11/2003 | Kreutzer |
| 6,660,876 B2 | 12/2003 | Gagne |
| 6,660,877 B2 | 12/2003 | Lenges |
| 6,737,539 B2 | 5/2004 | Lenges |
| 6,753,440 B2 | 6/2004 | Druliner |
| 6,770,770 B1 | 8/2004 | Baumann et al. |
| 6,812,352 B2 | 11/2004 | Kreutzer |
| 6,844,289 B2 | 1/2005 | Jackson |
| 6,846,945 B2 | 1/2005 | Lenges |
| 6,852,199 B2 | 2/2005 | Jungkamp et al. |
| 6,855,799 B2 | 2/2005 | Tam |
| 6,893,996 B2 | 5/2005 | Chu |
| 6,897,329 B2 | 5/2005 | Jackson |
| 6,906,218 B2 | 6/2005 | Allgeier |
| 6,924,345 B2 | 8/2005 | Gagne |
| 6,936,171 B2 | 8/2005 | Jackson |
| 6,984,604 B2 | 1/2006 | Cobb |
| 7,022,866 B2 | 4/2006 | Bartsch et al. |
| 7,067,685 B2 | 6/2006 | Bartsch et al. |
| 7,071,365 B2 | 7/2006 | Lu |
| 7,084,293 B2 | 8/2006 | Rosier et al. |
| 7,084,294 B2 | 8/2006 | Jungkamp et al. |
| 7,098,358 B2 | 8/2006 | Burattin et al. |
| 7,105,696 B2 | 9/2006 | Burattin et al. |
| 7,253,298 B2 | 8/2007 | Galland et al. |
| 7,345,006 B2 | 3/2008 | Bartsch et al. |
| 7,381,845 B2 | 6/2008 | Weiskopf et al. |
| 7,439,381 B2 | 10/2008 | Jungkamp et al. |
| 7,442,825 B2 | 10/2008 | Galland et al. |
| 7,470,805 B2 | 12/2008 | Rosier et al. |
| 7,521,575 B2 | 4/2009 | Bartsch et al. |
| 7,528,275 B2 | 5/2009 | Bartsch et al. |
| 7,538,240 B2 | 5/2009 | Jungkamp et al. |
| 7,541,486 B2 | 6/2009 | Scheidel et al. |
| 7,700,795 B2 | 4/2010 | Haderlein et al. |
| 2003/0100802 A1 | 5/2003 | Shapiro |
| 2003/0135014 A1 | 7/2003 | Radu et al. |
| 2003/0212298 A1 | 11/2003 | Brasse et al. |
| 2004/0063991 A1 | 4/2004 | Burattin et al. |
| 2004/0106815 A1 | 6/2004 | Ritter |
| 2004/0176622 A1 | 9/2004 | Bartsch et al. |
| 2004/0235648 A1 | 11/2004 | Bartsch et al. |
| 2004/0260112 A1 | 12/2004 | Basset et al. |
| 2005/0059737 A1 | 3/2005 | Allgeier |
| 2005/0090677 A1 | 4/2005 | Bartsch et al. |
| 2005/0090678 A1 | 4/2005 | Bartsch et al. |
| 2005/0159614 A1 | 7/2005 | Allgeier |
| 2005/0247624 A1 | 11/2005 | Jungkamp et al. |
| 2006/0142609 A1 | 6/2006 | Bourgeois et al. |
| 2006/0175189 A1 | 8/2006 | Gerber et al. |
| 2006/0252955 A1 | 11/2006 | Rosier et al. |
| 2006/0258873 A1 | 11/2006 | Rosier et al. |
| 2006/0258874 A1 | 11/2006 | Bartsch et al. |
| 2006/0264651 A1 | 11/2006 | Bartsch et al. |
| 2007/0060766 A1 | 3/2007 | Bartsch et al. |
| 2007/0073071 A1 | 3/2007 | Haderlein et al. |
| 2007/0083057 A1 | 4/2007 | Haderlein et al. |
| 2007/0088173 A1 | 4/2007 | Haderlein et al. |
| 2007/0112215 A1 | 5/2007 | Jungkamp et al. |
| 2007/0155977 A1 | 7/2007 | Jungkamp et al. |
| 2007/0155978 A1 | 7/2007 | Jungkamp et al. |
| 2007/0155980 A1 | 7/2007 | Scheidel et al. |
| 2007/0219386 A1 | 9/2007 | Ritter |
| 2008/0015378 A1 | 1/2008 | Foo |
| 2008/0015379 A1 | 1/2008 | Garner |
| 2008/0015380 A1 | 1/2008 | Foo |

| | | | |
|---|---|---|---|
| 2008/0015381 A1 | 1/2008 | Foo | |
| 2008/0015382 A1 | 1/2008 | Foo | |
| 2008/0071105 A1 | 3/2008 | Bartsch et al. | |
| 2008/0076944 A1 | 3/2008 | Bartsch et al. | |
| 2008/0083607 A1 | 4/2008 | Deckert et al. | |
| 2008/0221351 A1 | 9/2008 | Bartsch et al. | |
| 2008/0227214 A1 | 9/2008 | Jungkamp et al. | |
| 2008/0227998 A1 | 9/2008 | Scheidel et al. | |
| 2008/0242883 A1 | 10/2008 | Jungkamp et al. | |
| 2008/0242885 A1 | 10/2008 | Jungkamp et al. | |
| 2008/0242886 A1 | 10/2008 | Bartsch et al. | |
| 2008/0275266 A1 | 11/2008 | Bartsch et al. | |
| 2008/0281119 A1 | 11/2008 | Scheidel et al. | |
| 2008/0281120 A1 | 11/2008 | Jungkamp et al. | |
| 2009/0054671 A1 | 2/2009 | Haderlein et al. | |

FOREIGN PATENT DOCUMENTS

| | | |
|---|---|---|
| AU | 199665220 A | 2/1997 |
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159106 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 C | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |
| CN | 1266424 A | 9/2000 |
| CN | 1270543 A | 10/2000 |
| CN | 1068307 C | 7/2001 |
| CN | 1304334 A | 7/2001 |
| CN | 1069310 C | 8/2001 |
| CN | 1072980 C | 10/2001 |
| CN | 1076342 C | 12/2001 |
| CN | 1327881 A | 12/2001 |
| CN | 1331843 A | 1/2002 |
| CN | 1333745 A | 1/2002 |
| CN | 1082946 C | 4/2002 |
| CN | 1344180 A | 4/2002 |
| CN | 1356335 A | 7/2002 |
| CN | 1387534 A | 12/2002 |
| CN | 1099912 C | 1/2003 |
| CN | 1390241 A | 1/2003 |
| CN | 1103613 C | 3/2003 |
| CN | 1106218 C | 4/2003 |
| CN | 1108643 C | 5/2003 |
| CN | 1427807 A | 7/2003 |
| CN | 1449400 A | 10/2003 |
| CN | 1461295 A | 12/2003 |
| CN | 1471510 A | 1/2004 |
| CN | 1141285 C | 3/2004 |
| CN | 1142224 C | 3/2004 |
| CN | 1144781 C | 4/2004 |
| CN | 1487917 A | 4/2004 |
| CN | 1152855 C | 6/2004 |
| CN | 1535179 A | 10/2004 |
| CN | 1564807 A | 1/2005 |
| CN | 1568225 A | 1/2005 |
| CN | 1568226 A | 1/2005 |
| CN | 1617892 A | 5/2005 |
| CN | 1617900 A | 5/2005 |
| CN | 1212293 C | 7/2005 |
| CN | 1639176 A | 7/2005 |
| CN | 1213051 C | 8/2005 |
| CN | 1665776 A | 9/2005 |
| CN | 1670139 A | 9/2005 |
| CN | 1674989 A | 9/2005 |
| CN | 1675172 A | 9/2005 |
| CN | 1222358 C | 10/2005 |
| CN | 1732148 A | 2/2006 |
| CN | 1735460 A | 2/2006 |
| CN | 1245489 C | 3/2006 |
| CN | 1740183 A | 3/2006 |
| CN | 1745062 A | 3/2006 |
| CN | 1767895 A | 5/2006 |
| CN | 1260009 C | 6/2006 |
| CN | 12666424 C | 7/2006 |
| CN | 1270543 C | 8/2006 |
| CN | 1274671 C | 9/2006 |
| CN | 1274699 C | 9/2006 |
| CN | 1835915 A | 9/2006 |
| CN | 1279088 C | 10/2006 |
| CN | 1847288 A | 10/2006 |
| CN | 1283620 C | 11/2006 |
| CN | 1857775 A | 11/2006 |
| CN | 1289539 C | 12/2006 |
| CN | 1293942 C | 1/2007 |
| CN | 1906150 A | 1/2007 |
| CN | 1914154 A | 2/2007 |
| CN | 1914155 A | 2/2007 |
| CN | 1914156 A | 2/2007 |
| CN | 1914157 A | 2/2007 |
| CN | 1914158 A | 2/2007 |
| CN | 1914159 A | 2/2007 |
| CN | 1914160 A | 2/2007 |
| CN | 1914161 A | 2/2007 |
| CN | 1914162 A | 2/2007 |
| CN | 1914165 A | 2/2007 |
| CN | 1914166 A | 2/2007 |
| CN | 1914167 A | 2/2007 |
| CN | 1914216 A | 2/2007 |
| CN | 1307237 C | 3/2007 |
| CN | 1315790 C | 5/2007 |
| CN | 1318432 C | 5/2007 |
| CN | 1997624 A | 7/2007 |
| CN | 1331843 C | 8/2007 |
| CN | 101020641 A | 8/2007 |
| CN | 101035799 A | 9/2007 |
| CN | 101043946 A | 9/2007 |
| CN | 100348322 C | 11/2007 |
| CN | 100351227 C | 11/2007 |
| CN | 100352824 C | 12/2007 |
| CN | 100361966 C | 1/2008 |
| CN | 100364666 C | 1/2008 |
| DE | 1807088 U | 3/1960 |
| DE | 1807088 A1 | 6/1969 |
| DE | 2055747 A1 | 5/1971 |
| DE | 1593277 B2 | 8/1973 |
| DE | 1593277 C3 | 3/1974 |
| DE | 2700904 C2 | 10/1983 |
| DE | 68909466 T2 | 3/1994 |
| DE | 10136488 A1 | 2/2003 |
| DE | 10150285 A1 | 4/2003 |
| DE | 10350999 A1 | 6/2005 |
| DE | 102004004696 A1 | 8/2005 |
| EP | 0001899 B1 | 3/1982 |
| EP | 123438 B1 | 7/1987 |
| EP | 160296 B1 | 10/1988 |
| EP | 268448 B1 | 9/1991 |
| EP | 510689 A1 | 10/1992 |
| EP | 248643 B1 | 3/1993 |
| EP | 336314 B1 | 9/1993 |
| EP | 464691 B1 | 12/1993 |
| EP | 675871 B1 | 4/1997 |
| EP | 634395 B1 | 9/1997 |
| EP | 650959 B1 | 9/1997 |
| EP | 784610 B1 | 2/1999 |
| EP | 757672 B1 | 6/1999 |
| EP | 792259 B1 | 8/1999 |
| EP | 804412 B1 | 12/1999 |
| EP | 1000019 A1 | 5/2000 |
| EP | 1001928 A1 | 5/2000 |
| EP | 1003716 A1 | 5/2000 |

| | | | | | | |
|---|---|---|---|---|---|---|
| EP | 1019190 | A1 | 7/2000 | GB | 1429621 | A | 3/1976 |
| EP | 755302 | B1 | 10/2000 | GB | 1436932 | A | 5/1976 |
| EP | 929513 | B1 | 4/2001 | GB | 1458322 | A | 12/1976 |
| EP | 881924 | B1 | 5/2001 | GB | 1482909 | A | 8/1977 |
| EP | 854858 | B1 | 6/2001 | GB | 2007521 | A | 5/1979 |
| EP | 815073 | B1 | 7/2001 | GB | 1565443 | A | 4/1980 |
| EP | 1144114 | A3 | 9/2001 | GB | 1594694 | A | 8/1981 |
| EP | 1091804 | B1 | 2/2002 | GB | 2007521 | B | 6/1982 |
| EP | 944585 | B1 | 4/2002 | HK | 1025950 | A1 | 7/2003 |
| EP | 10000019 | B1 | 2/2003 | HK | 1026383 | A1 | 7/2004 |
| EP | 911339 | B1 | 4/2003 | HK | 1052364 | A1 | 5/2007 |
| EP | 1216268 | B1 | 11/2003 | JP | 48028423 | Y1 | 8/1973 |
| EP | 1350788 | A3 | 11/2003 | JP | 48028423 | B | 9/1973 |
| EP | 1003607 | B1 | 12/2003 | JP | 49043924 | Y1 | 12/1974 |
| EP | 1003716 | B1 | 2/2004 | JP | 50059324 | U | 6/1975 |
| EP | 1313743 | B1 | 3/2004 | JP | 50059326 | U | 6/1975 |
| EP | 1414567 | A1 | 5/2004 | JP | 51007649 | B | 3/1976 |
| EP | 1427695 | A1 | 6/2004 | JP | 52012698 | B | 4/1977 |
| EP | 1438133 | A1 | 7/2004 | JP | 1013127 | C | 9/1980 |
| EP | 1019190 | B1 | 12/2004 | JP | 55047031 | B | 11/1980 |
| EP | 1140801 | B1 | 2/2005 | JP | 57156454 | U | 10/1982 |
| EP | 1395547 | B1 | 3/2005 | JP | 57156455 | U | 10/1982 |
| EP | 1001928 | B1 | 4/2005 | JP | 57179144 | U | 11/1982 |
| EP | 1521736 | A1 | 4/2005 | JP | 1136333 | C | 2/1983 |
| EP | 1521737 | A1 | 4/2005 | JP | 58067658 | U | 5/1983 |
| EP | 1521738 | A2 | 4/2005 | JP | 58126892 | U | 5/1983 |
| EP | 1603865 | A1 | 12/2005 | JP | 1170710 | C | 10/1983 |
| EP | 1324976 | B1 | 2/2006 | JP | 58159452 | U | 10/1983 |
| EP | 1214975 | B1 | 3/2006 | JP | 60044295 | A | 3/1985 |
| EP | 13249778 | B1 | 3/2006 | JP | 60044295 | B | 10/1985 |
| EP | 1648860 | A1 | 4/2006 | JP | 62294691 | A | 12/1987 |
| EP | 891323 | B1 | 6/2006 | JP | 63135363 | U | 9/1988 |
| EP | 1226147 | B1 | 6/2006 | JP | 1013127 | Y2 | 4/1989 |
| EP | 1438317 | B1 | 6/2006 | JP | 1209830 | A | 8/1989 |
| EP | 1682561 | A1 | 7/2006 | JP | 1136333 | U | 9/1989 |
| EP | 1448668 | B1 | 8/2006 | JP | 1050220 | B | 10/1989 |
| EP | 1587621 | B1 | 8/2006 | JP | 1173751 | U | 12/1989 |
| EP | 1713759 | A1 | 10/2006 | JP | 1565159 | C | 6/1990 |
| EP | 1713761 | A1 | 10/2006 | JP | 3001298 | B | 1/1991 |
| EP | 1713762 | A1 | 10/2006 | JP | 1615749 | C | 8/1991 |
| EP | 1713766 | A1 | 10/2006 | JP | 3205587 | A | 9/1991 |
| EP | 1716102 | A2 | 11/2006 | JP | 1627124 | C | 11/1991 |
| EP | 1716103 | A1 | 11/2006 | JP | 1627146 | C | 11/1991 |
| EP | 1716104 | A1 | 11/2006 | JP | 3069915 | B | 11/1991 |
| EP | 1716105 | A1 | 11/2006 | JP | 3285878 | A | 12/1991 |
| EP | 1716106 | A1 | 11/2006 | JP | 1642102 | C | 2/1992 |
| EP | 1716107 | A1 | 11/2006 | JP | 4012248 | Y2 | 3/1992 |
| EP | 1716109 | A2 | 11/2006 | JP | 4057050 | U | 5/1992 |
| EP | 1610893 | B1 | 3/2007 | JP | 4166155 | A | 6/1992 |
| EP | 1621531 | B1 | 3/2007 | JP | 4230254 | A | 8/1992 |
| EP | 1438132 | B1 | 4/2007 | JP | 4057050 | B | 9/1992 |
| EP | 1799697 | A1 | 6/2007 | JP | 4060532 | B | 9/1992 |
| EP | 1713764 | B1 | 8/2007 | JP | 4118676 | U | 10/1992 |
| EP | 1713816 | B1 | 8/2007 | JP | 4128141 | U | 11/1992 |
| EP | 1825914 | A1 | 8/2007 | JP | 1729140 | C | 1/1993 |
| EP | 1448620 | B1 | 6/2008 | JP | 1811422 | C | 12/1993 |
| EP | 1817108 | B1 | 6/2008 | JP | 7025841 | Y2 | 6/1995 |
| EP | 1713760 | B1 | 7/2008 | JP | 7188144 | A | 7/1995 |
| EP | 1571172 | B1 | 10/2008 | JP | 2037346 | C | 3/1996 |
| EP | 1988998 | A1 | 11/2008 | JP | 8504814 | A | 5/1996 |
| EP | 1265832 | B1 | 5/2009 | JP | 8157795 | A | 6/1996 |
| EP | 1592659 | B1 | 7/2009 | JP | 2098106 | C | 10/1996 |
| EP | 1586598 | B1 | 9/2009 | JP | 025217777 | Y2 | 1/1997 |
| EP | 2098106 | A1 | 9/2009 | JP | 02623448 | B2 | 6/1997 |
| EP | 1567478 | B1 | 10/2009 | JP | 9505586 | A | 6/1997 |
| EP | 1682559 | B1 | 12/2009 | JP | 9512013 | A | 12/1997 |
| EP | 1630166 | B1 | 2/2010 | JP | 10505101 | A | 5/1998 |
| FR | 1544656 | A | 11/1968 | JP | 10506911 | A | 7/1998 |
| FR | 2015115 | A5 | 4/1970 | JP | 10509954 | A | 9/1998 |
| FR | 1603513 | A | 5/1971 | JP | 02818503 | B2 | 10/1998 |
| FR | 2069411 | A5 | 9/1971 | JP | 10512879 | A | 12/1998 |
| FR | 2845379 | B1 | 12/2004 | JP | 11501660 | A | 2/1999 |
| FR | 2873696 | A1 | 2/2006 | JP | 11504262 | A | 4/1999 |
| FR | 2873696 | B1 | 10/2006 | JP | 02911608 | B2 | 6/1999 |
| GB | 0219474 | A | 7/1924 | JP | 11507297 | A | 6/1999 |
| GB | 1104140 | A | 2/1968 | JP | 03001298 | B2 | 1/2000 |
| GB | 1203702 | A | 9/1970 | JP | 03069915 | B2 | 7/2000 |
| GB | 1213175 | A | 11/1970 | JP | 2001500135 | A | 1/2001 |
| GB | 1429169 | A | 3/1976 | JP | 2001506250 | A | 5/2001 |

| | | | | | | | |
|---|---|---|---|---|---|---|---|
| JP | 2001512097 | A | 8/2001 | TW | 455576 | B | 9/2001 |
| JP | 03205587 | B2 | 9/2001 | TW | 457244 | B | 10/2001 |
| JP | 2001516640 | A | 10/2001 | TW | 458959 | B | 10/2001 |
| JP | 03285878 | B2 | 5/2002 | TW | 519496 | B | 2/2003 |
| JP | 2002517473 | A | 6/2002 | TW | 527340 | B | 4/2003 |
| JP | 03320424 | B2 | 9/2002 | TW | 576837 | B | 2/2004 |
| JP | 2002533321 | A | 10/2002 | TW | 580489 | B | 3/2004 |
| JP | 03380543 | B2 | 2/2003 | TW | 580490 | B | 3/2004 |
| JP | 2003510385 | A | 3/2003 | TW | 584623 | B | 4/2004 |
| JP | 2003526688 | A | 9/2003 | TW | 592821 | B | 6/2004 |
| JP | 03478399 | B2 | 12/2003 | TW | 226345 | B | 1/2005 |
| JP | 2004501058 | A | 1/2004 | TW | 233438 | B | 6/2005 |
| JP | 2004507550 | A | 3/2004 | TW | 245780 | B | 12/2005 |
| JP | 03519410 | B2 | 4/2004 | TW | 266650 | B | 11/2006 |
| JP | 03535172 | B2 | 6/2004 | WO | WO7900193 | A1 | 4/1979 |
| JP | 03553952 | B2 | 8/2004 | WO | WO9414752 | A1 | 7/1994 |
| JP | 2004534032 | A | 11/2004 | WO | WO9514659 | A1 | 6/1995 |
| JP | 2004535929 | A | 12/2004 | WO | WO9528228 | A1 | 10/1995 |
| JP | 03621133 | B2 | 2/2005 | WO | WO9529153 | A1 | 11/1995 |
| JP | 2005503410 | A | 2/2005 | WO | WO9611185 | A1 | 4/1996 |
| JP | 2005505610 | A | 2/2005 | WO | WO9616022 | A1 | 5/1996 |
| JP | 2005505611 | A | 2/2005 | WO | WO9622968 | A1 | 8/1996 |
| JP | 2005510588 | A | 4/2005 | WO | WO9629303 | A1 | 9/1996 |
| JP | 2005510605 | A | 4/2005 | WO | WO9703040 | A1 | 1/1997 |
| JP | 2004509942X | | 10/2005 | WO | WO9712857 | A1 | 4/1997 |
| JP | 2005533095 | A | 11/2005 | WO | WO9724183 | A1 | 7/1997 |
| JP | 2005533096 | A | 11/2005 | WO | WO9736855 | A2 | 10/1997 |
| JP | 2005538075 | A | 12/2005 | WO | WO9811051 | A1 | 3/1998 |
| JP | 03739404 | B2 | 1/2006 | WO | WO9827054 | A1 | 6/1998 |
| JP | 2004534032X | | 1/2006 | WO | WO9906146 | A2 | 2/1999 |
| JP | 2004535929X | | 1/2006 | WO | WO9906356 | | 2/1999 |
| JP | 2006000451 | A | 1/2006 | WO | WO9906359 | A1 | 2/1999 |
| JP | 2006511591 | A | 4/2006 | WO | WO9913983 | A1 | 3/1999 |
| JP | 2006519797 | A | 8/2006 | WO | WO9964155 | A1 | 12/1999 |
| JP | 2006528616 | A | 12/2006 | WO | WO0001485 | A2 | 1/2000 |
| JP | 2007083057 | A | 4/2007 | WO | WO0037431 | A1 | 6/2000 |
| JP | 2007509885 | A | 4/2007 | WO | WO0121684 | A1 | 3/2001 |
| JP | 2007509886 | A | 4/2007 | WO | WO0136429 | A1 | 5/2001 |
| JP | 2007509887 | A | 4/2007 | WO | WO0168247 | A2 | 9/2001 |
| JP | 2007519516 | A | 7/2007 | WO | WO0168247 | A8 | 9/2001 |
| JP | 2007519663 | A | 7/2007 | WO | WO0211108 | A1 | 2/2002 |
| JP | 2007519664 | A | 7/2007 | WO | WO0213964 | A2 | 2/2002 |
| JP | 2007519666 | A | 7/2007 | WO | WO0218392 | A1 | 3/2002 |
| JP | 2007519667 | A | 7/2007 | WO | WO0226698 | A1 | 4/2002 |
| JP | 2007519670 | A | 7/2007 | WO | WO0230854 | A2 | 4/2002 |
| JP | 2007519671 | A | 7/2007 | WO | WO02053527 | A1 | 7/2002 |
| JP | 2007519672 | A | 7/2007 | WO | WO02092551 | A2 | 11/2002 |
| JP | 2007519673 | A | 7/2007 | WO | WO 03/011457 | A1 * | 2/2003 |
| JP | 2007519674 | A | 7/2007 | WO | WO03011457 | A1 | 2/2003 |
| JP | 2007519675 | A | 7/2007 | WO | WO03018540 | A1 | 3/2003 |
| JP | 2007519677 | A | 7/2007 | WO | WO03024919 | A1 | 3/2003 |
| JP | 2007522122 | A | 8/2007 | WO | WO03031392 | A1 | 4/2003 |
| JP | 04012248 | B2 | 11/2007 | WO | WO03033141 | A1 | 4/2003 |
| JP | 2006515323X | | 2/2008 | WO | WO03033509 | A1 | 4/2003 |
| JP | 04057050 | B2 | 3/2008 | WO | WO03046019 | A1 | 6/2003 |
| JP | 04060532 | B2 | 3/2008 | WO | WO03046049 | A1 | 6/2003 |
| JP | 2006512918X | | 3/2008 | WO | WO03068729 | A1 | 8/2003 |
| JP | 2008515831 | A | 5/2008 | WO | WO03076394 | A1 | 9/2003 |
| JP | 2008516907 | A | 5/2008 | WO | WO2004007431 | A1 | 1/2004 |
| JP | 04118676 | B2 | 7/2008 | WO | WO2004007432 | A1 | 1/2004 |
| JP | 04128141 | B2 | 7/2008 | WO | WO2004007435 | A2 | 1/2004 |
| JP | 04166155 | B2 | 10/2008 | WO | WO2004007508 | A2 | 1/2004 |
| JP | 04230254 | B2 | 2/2009 | WO | WO2004060855 | A1 | 7/2004 |
| KR | 198802621 | Y1 | 7/1988 | WO | WO2004064994 | A2 | 8/2004 |
| KR | 198802296 | B | 10/1988 | WO | WO2004065352 | A2 | 8/2004 |
| KR | 198802296 | B1 | 10/1988 | WO | WO2004080924 | A2 | 9/2004 |
| KR | 199003458 | B1 | 5/1990 | WO | WO2004080948 | A1 | 9/2004 |
| KR | 199008166 | B1 | 11/1990 | WO | WO2004087314 | A1 | 10/2004 |
| KR | 199104132 | B1 | 6/1991 | WO | WO2005019160 | A1 | 3/2005 |
| KR | 199205087 | Y1 | 7/1992 | WO | WO2005042156 | A1 | 5/2005 |
| KR | 2006132885 | A | 12/2006 | WO | WO2005042157 | A2 | 5/2005 |
| MX | 2004PA002764 | A | 6/2004 | WO | WO2005042547 | A1 | 5/2005 |
| NL | 197700262 | A | 7/1977 | WO | WO2005042549 | A1 | 5/2005 |
| NL | 188158 | C | 4/1992 | WO | WO2005073166 | A3 | 8/2005 |
| SU | 677650 | A | 7/1979 | WO | WO2005073167 | A1 | 8/2005 |
| TW | 387874 | B | 4/2000 | WO | WO2005073168 | A1 | 8/2005 |
| TW | 400249 | B | 8/2000 | WO | WO2005073169 | A1 | 8/2005 |
| TW | 453983 | B | 9/2001 | WO | WO2005073170 | A1 | 8/2005 |
| TW | 453985 | B | 9/2001 | WO | WO2005073171 | A1 | 8/2005 |

| | | |
|---|---|---|
| WO | WO2005073172 A1 | 8/2005 |
| WO | WO2005073173 A1 | 8/2005 |
| WO | WO2005073174 A1 | 8/2005 |
| WO | WO2005073175 A1 | 8/2005 |
| WO | WO2005073176 A1 | 8/2005 |
| WO | WO2005073178 A2 | 8/2005 |
| WO | WO2005073179 A1 | 8/2005 |
| WO | WO2005073241 A1 | 8/2005 |
| WO | WO2006040023 A1 | 4/2006 |
| WO | WO2006042675 A2 | 4/2006 |
| WO | WO2007051374 A1 | 5/2007 |
| WO | WO2007096274 A1 | 8/2007 |
| WO | WO 2007115936 | 10/2007 |
| WO | WO2007115936 A2 | 10/2007 |
| WO | WO2008008926 A2 | 1/2008 |
| WO | WO2008008928 A2 | 1/2008 |
| WO | WO2008008929 A2 | 1/2008 |
| WO | WO2008008930 A2 | 1/2008 |
| WO | WO2008028843 A1 | 3/2008 |
| WO | WO2008062058 A1 | 5/2008 |

* cited by examiner

PROCESS FOR THE PREPARATION OF DINITRILES

This application is an application under 35 U.S.C. Section 371 of International Application Number PCT/FR2004/001108 filed on May 07, 2004.

The present invention relates to a process for the preparation of dinitriles by hydrocyanation of unsaturated nitrile compounds in the presence of a catalyst based on a metal element in the zero oxidation state and on organophosphorus ligands.

It relates more particularly to a process for the recovery from the hydrocyanation medium of a catalyst for the hydrocyanation of unsaturated nitrites to dinitriles.

The hydrocyanation reaction is used industrially for the synthesis of compounds comprising nitrile function groups from compounds comprising unsaturations. Thus, adiponitrile, which is an important chemical intermediate, in particular in the manufacture of hexamethylenediamine, a monomer for a number of polymers, such as polyamide, is manufactured by hydrocyanation in two stages of butadiene or of a hydrocarbon cut, known as the C4 cut, comprising butadiene. In this manufacturing process, the two reactions are carried out with catalytic systems composed essentially of the same entities, namely an organometallic coordination complex and at least one organophosphorus ligand of monodentate organophosphite type, such as tritolyl phosphite.

Numerous patents disclose this process for the manufacture of adiponitrile, and processes for the manufacture of the catalysts.

Furthermore, for the economics of the process, it is important to be able to recover the catalytic system and to recycle it in the hydrocyanation stages.

Thus, U.S. Pat. No. 4,539,302 discloses a process for the recovery of the catalyst from the reaction medium obtained in the second stage of the process of the preparation of adiponitrile, namely hydrocyanation of unsaturated nitrites to dinitriles.

This process for recovery by settling makes it possible to limit the losses of metal element and facilitates the control of the organophosphorus ligand/metal element ratio, which is low for the hydrocyanation of unsaturated nitrites. Thus, it is also possible to recover a catalytic system with a high ligand/metal element ratio, which makes possible recycling and reuse of the catalytic system in stages for the manufacture of catalyst and/or in stages for the hydrocyanation of butadiene or the isomerization of branched pentenenitriles.

Numerous other organophosphorus ligands have been provided for the catalysis of these hydrocyanation reactions.

Thus, bidentate ligands of organophosphite, organophosphinite, organophosphonite and organophosphine type have been disclosed in numerous patents, such as, for example, Patents WO 99/06355, WO 99/06356, WO 99/06357, WO 99/06358, WO 99/52632, WO 99/65506, WO 99/62855, US 5 693 843, WO 96/1182, WO 96/22968, U.S. Pat. No. 5 981 772, WO 01/36429, WO 99/64155 or WO 02/13964.

Finally, provision has also been made, by Patent WO 03/11457, to use a mixture of mono- and bidentate ligands for the catalysis of hydrocyanation reactions. The use of such a mixture makes it possible to facilitate the synthesis of the catalyst and the formation of the organometallic complex, in particular with respect to processes for the synthesis of organometallic complexes with bidentate ligands.

In the case of mixtures of ligands, it is also important to be able to recover the catalyst without losing ligands or metal element.

One of the aims of the present invention is to provide, in a process for the preparation of dinitriles, a process for the recovery of a catalyst formed by a mixture of mono- and bidentate ligands and to be able to reuse the catalyst thus recovered in the hydrocyanation and/or isomerization stages.

To this end, the invention provides a process for the preparation of dinitrile compounds by hydrocyanation of unsaturated mononitrile compounds in the presence of a catalytic system comprising an organometallic complex formed from a metal element and from a mixture of organophosphorus ligands comprising at least one monodentate organophosphite compound and at least one bidentate organophosphorus compound chosen from the group consisting of organophosphites, organophosphinites, organophosphonites and organophosphines, and optionally a promoter, the said process comprising a recovery of the catalytic system, characterized in that the process consists in controlling the concentration of unsaturated nitrites in the reaction medium resulting from the hydrocyanation reaction in order to obtain a concentration by weight of unsaturated nitrites of less than 20% in the said medium, in feeding the said medium to a stage of settling into two upper and lower phases, and in separating the two phases, the lower phase being at least partially recycled to the said hydrocyanation stage and the upper phase being subjected to a liquid/liquid extraction in order to separate the organometallic complex and the organophosphorus compounds present in the said upper phase from the dinitriles.

Mention may be made, as monodentate organophosphite ligand suitable for the invention, by way of examples, of triphenyl phosphite, tritolyl phosphite (TTP) or tricymenyl phosphite.

Mention may be made, as bidentate ligands which are suitable for the invention, of the compounds with the following structures, in which Ph means phenyl:

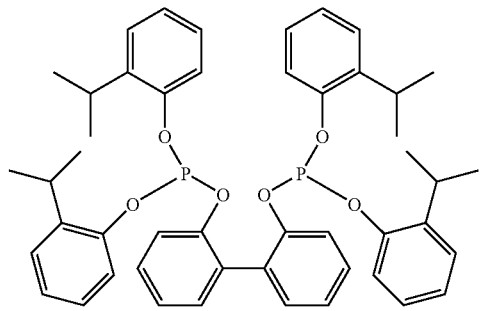

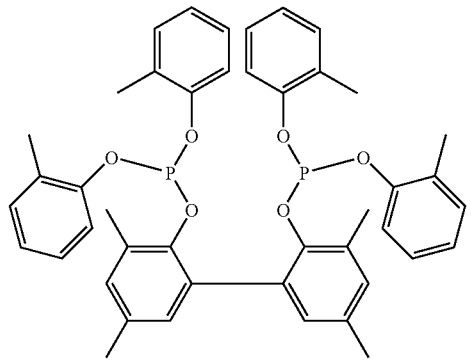

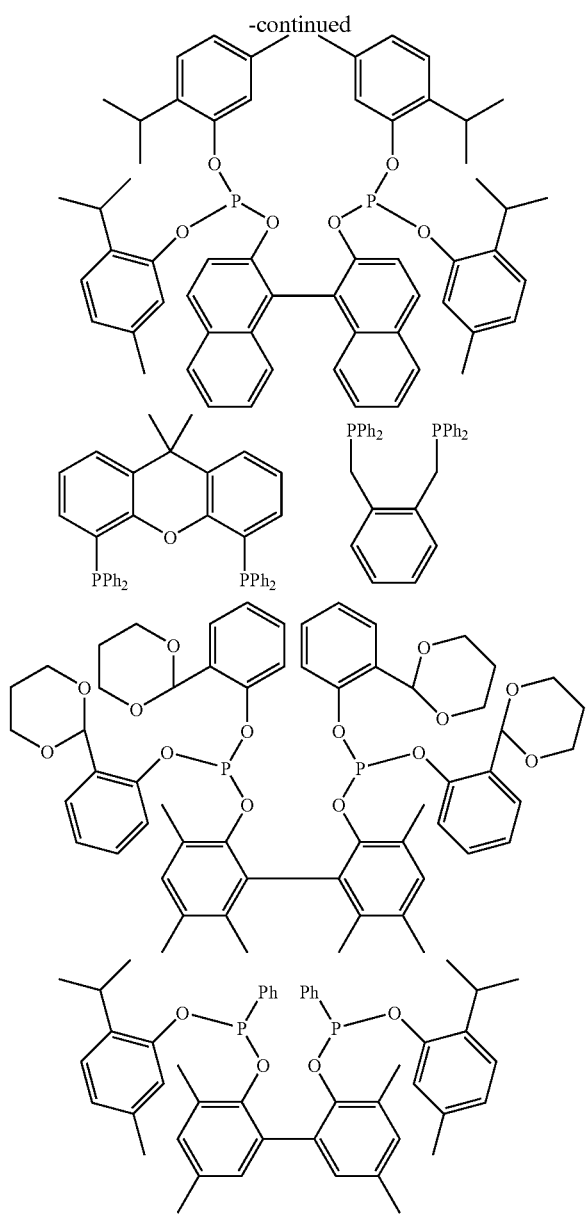

According to a preferred characteristic of the invention, the catalyst present in the reaction medium generally comprises a number of moles of bidentate ligand, expressed as number of phosphorus atoms with respect to a metal element atom, of between 1 and 4, while that of monodentate ligand, expressed as number of phosphorus atoms, is between 4 and 7.

In the present text, the expression "ligand/nickel" always refers to the ratio of all the molecules of mono- and/or bidentate ligands with respect to the number of nickel atoms, unless expressly indicated otherwise.

The metal elements exhibiting a catalytic effect in a hydrocyanation reaction are, for example, nickel, cobalt, iron, ruthenium, rhodium, palladium, osmium, iridium, platinum, copper, silver, gold, zinc, cadmium or cerium. Nickel is the preferred catalytic element. For greater clarity, the metal element will be denoted by the term "nickel" in the continuation of the present text, without this being a limiting meaning.

Furthermore, in the hydrocyanation reaction of the unsaturated nitrites, a promoter or cocatalyst is generally used. Lewis acids are generally used as preferred promoters.

Use may in particular be made, by way of examples, of the Lewis acids cited in the work edited by G. A. Olah, "Friedel-Crafts and Related Reactions", Volume I, pages 191 to 197 (1963).

The Lewis acids which can be employed as cocatalysts in the present process are advantageously chosen from compounds of the elements from Groups Ib, IIb, IIIa, IIIb, IVa, IVb, Va, Vb, VIb, VIIb and VIII of the Periodic Table of the Elements. These compounds are generally salts, in particular halides, such as chlorides or bromides, sulphates, sulphonates, haloalkylsulphonates, perhaloalkylsulphonates, in particular fluoroalkylsulphonates or perfluoroalkyl-sulphonates, haloacetates, perhaloacetates, carboxylates and phosphates.

Mention may be made, as non-limiting examples of such Lewis acids, of zinc chloride, zinc bromide, zinc iodide, manganese chloride, manganese bromide, cadmium chloride, cadmium bromide, stannous chloride, stannous bromide, stannous sulphate, stannous tartrate, indium chloride, indium trifluoromethylsulphonate, indium trifluoroacetate, the chlorides or bromides of rare earth elements, such as lanthanum, cerium, praseodymium, neodymium, samarium, europium, gadolinium, terbium, dysprosium, hafnium, erbium, thulium, ytterbium and lutetium, cobalt chloride, ferrous chloride or yttrium chloride.

Use may also be made, as Lewis acid, of compounds such as triphenylborane or titanium tetraisopropoxide.

It is possible, of course, to employ mixtures of several Lewis acids.

Preference is very particularly given, among Lewis acids, to zinc chloride, zinc bromide, stannous chloride, stannous bromide, triphenylborane, indium trifluoromethylsulphonate, indium trifluoroacetate and zinc chloride/stannous chloride mixtures.

The Lewis acid cocatalyst employed generally represents from 0.005 to 50 mol per mole of nickel.

According to a preferred characteristic of the invention, the medium fed to the settling stage is cooled to a temperature of between 25° C. and 75° C., advantageously between 30° C. and 55° C.

In order to obtain settling and separation into two phases of the reaction medium, it is advantageous for the concentration by weight of nickel in the reaction medium fed to the settling stage to be between 0.2 and 2%.

In order to obtain such a nickel concentration, it may be necessary to add a certain amount of catalytic system to the reaction medium exiting from the hydrocyanation stage. This is because the concentration of nickel used in the reaction medium when the nickel is used in combination with a bidentate ligand may be very low, such as, for example, of the order of 100 to 2000 mg of nickel/kg of reaction medium.

According to a preferred embodiment of the invention, the concentration of nickel in the medium resulting from the hydrocyanation stage is adjusted to a suitable and desired value by introduction of at least a portion of the lower phase obtained in the settling stage.

According to yet another preferred characteristic of the invention, the concentration of unsaturated nitrites in the medium fed to the settling stage is less than or equal to 20% by weight, advantageously between 4 and 20% by weight.

The control or the production of such a concentration can be carried out in different ways:

A first possibility is to control and define the degree of conversion of the unsaturated nitrites in the hydrocyanation stage in order to obtain, in the reaction medium at the end of the reaction or exiting from the said reactor, a concentration of unsaturated nitrites of less than or equal to 20% by weight.

According to another embodiment of the invention, the reaction medium exiting from the hydrocyanation stage is fed to a stage of distillation under reduced pressure or flashing of the unconverted unsaturated nitriles. This stage makes it possible to control the concentration of the unsaturated nitriles in the medium fed to the settling stage.

To avoid losses of nickel by precipitation in the distillation bottoms, it is advantageous for the bottom temperature of this distillation stage to be less than 140° C. The term "distillation bottom temperature" is understood to mean the temperature of the medium which is found in the boiler but also the temperature of the walls of the said boiler.

In this embodiment comprising the stage of distillation of a portion of the unsaturated nitrites, the adjusting or control of the concentration of nickel in the distillation bottoms fed to the settling stage can be carried out by recycling a portion of the lower phase from the settling. This recycling is advantageously carried out before feeding the medium to the distillation stage.

According to the process of the invention, the lower phase obtained in the decanter or heavy phase comprises most of the nickel and of the bidentate ligand, and a portion of the monodentate ligand. However, as the coefficients for partition of the metal element and of the organophosphorus ligands between the two phases are different, the molar ratio of ligands/metal element atoms will be low in the lower phase and high in the upper phase. In addition, the process of the invention makes it possible to use most of the bidentate ligand preferentially in the stage of hydrocyanation of the unsaturated nitrites to thus obtain a high selectivity for linear dinitriles.

According to another characteristic of the process of the invention, the upper phase recovered in the settling stage comprises a ligand/nickel molar ratio, expressed as number of phosphorus atoms, advantageously of greater than 8.

According to the invention, the total recovery of the catalyst and of the ligands is carried out by a liquid/liquid extraction of these using an extraction solvent which is immiscible with the dinitriles.

Mention may be made, as suitable extraction solvent, by way of examples, of saturated, linear or cyclic, aliphatic hydrocarbons, such as hexane, heptane, octane, cyclohexane, cyclopentane, cycloheptane and more generally cycloparaffins or analogues. Cyclohexane is the preferred extraction solvent.

After extraction, the cyclohexane solution of the organometallic complex and of the ligands is fed to a stage of evaporation or distillation of the extraction solvent. To limit the loss of nickel by precipitation, it is important for the ligand/nickel molar ratio, expressed as number of phosphorus atoms with respect to the number of nickel atoms, to be high and in particular greater than 8. This high ratio is, in the process of the invention, obtained in the settling stage by virtue of the coefficients of partition of the various chemical entities between the two upper and lower phases.

In addition, in order to limit losses of nickel, the bottom temperature of the stage of distillation or evaporation at atmospheric pressure or under a pressure of greater than atmospheric pressure is advantageously less than 180° C. The term "bottom temperature" is understood to mean the temperature of the medium present in the boiler of the said stage and the temperature of the walls of the said boiler.

The process for recovery of the catalyst of the invention thus makes possible complete recovery of the catalyst and of the organophosphorus ligands.

The invention applies generally to a process for the conversion of unsaturated mononitriles to dinitriles which constitutes the second stage of a process for the manufacture of dinitrile compounds by double hydrocyanation of diolefins, such as butadiene. This process comprises a first stage of hydrocyanation of the diolefin to unsaturated nitriles carried out with a catalyst which is advantageously composed of the same compounds as those of the catalytic system used in the second stage with, possibly, different ratios between the compounds. This first stage is generally combined with an isomerization reaction of the branched mononitriles formed in order to convert them to linear unsaturated mononitriles which will be fed to the second stage. This isomerization is carried out with a catalytic system equivalent to that of the first stage and in the absence of hydrogen cyanide.

In such a process comprising the two stages, the catalyst and the ligands recovered after evaporation of the extraction solvent are advantageously recycled, either in a stage of hydrocyanation of the diolefins (or of a C4 hydrocarbon cut) or in a stage of preparation of the catalyst, and/or to the isomerization of the branched unsaturated nitrites or alternatively added to the catalyst recovered from the lower settling phase before introduction into the stage of hydrocyanation of the unsaturated nitrile compounds.

In one embodiment of the invention, at least a portion of the catalyst recovered after evaporation of the extraction solvent is introduced into the stage of isomerization of the branched nitrites and then optionally into the stage of hydrocyanation of the dienes. The catalyst recovered after the latter stage can be recycled directly in the liquid/liquid extraction stage.

In this embodiment, the catalyst used in the isomerization stage and the stage of hydrocyanation of the dienes comprises a low proportion of bidentate ligand, thus making it possible to reduce the losses of this ligand due, for example, to a hydrolysis reaction or to a reaction with compounds present in the dienes, such as tert-butylcatechol (TBC) present in butadiene. The present invention preferably applies to the hydrocyanation of linear or branched unsaturated nitrites comprising from 3 to 8 carbon atoms and more preferably of 3-pentenenitrile and/or 4-pentenenitrile for the production of adiponitrile with use of a catalyst of the type represented by the following formula:

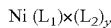

in which $L_1$ represents a monodentate ligand and $L_2$ a bidentate ligand, x and y represent decimal numbers ranging from 0 to 4, the sum x+2y being equal to 3 or 4.

The catalyst can be composed of a mixture of complexes corresponding to the above general formula.

The catalytic system or the reaction medium can also comprise an amount of mono- and/or bidentate organophosphorus ligand in the free form, that is to say not bonded to the nickel.

The catalytic systems of the invention can be obtained by formation, in a first stage, of an organometallic complex between the nickel and monodentate ligand. Processes for the formation of such complexes are, for example, disclosed in U.S. Pat. No. 3,903,120 and U.S. Pat. No. 4,416,825. In a second stage, the bidentate ligand is added to the medium comprising the said organometallic complex.

The first and second hydrocyanation stages are advantageously carried out in series. In this case, it is advantageous for at least a portion of the catalyst recovered, in particular that recovered in the liquid/liquid extraction, and more particularly the catalyst recovered in the upper phase of the settling stage, to be recycled and used as catalyst. in the first stage of hydrocyanation of butadiene and/or in the stage of isomerization of branched unsaturated nitrites to linear unsaturated nitrites. The use of an identical or similar catalytic system for the hydrocyanation of butadiene and that of pentenenitriles is preferred.

However, it is also possible to use the catalytic system described above solely in the stage of hydrocyanation of unsaturated nitriles, the catalytic system used in the first stage of hydrocyanation of butadiene and the isomerization stage being different, either in the nature of the compounds or in the ratio between the various compounds.

Other details and advantages of the invention will become more clearly apparent in the light of the examples given below solely by way of indication and illustration.

Abbreviations:
PN: pentenenitriles
DN: dinitriles (mixtures of dinitriles AdN, MGN and ESN, predominantly comprising AdN)
AdN: adiponitrile
MGN methylglutaronitrile
ESN: ethylsuccinonitrile

EXAMPLE 1

Hydrocyanation of pentenenitriles was carried out using a catalytic system comprising an organometallic complex obtained from nickel in the zero oxidation state, from a promoter $ZnCl_2$ and from organophosphorus compounds with the following formulae:

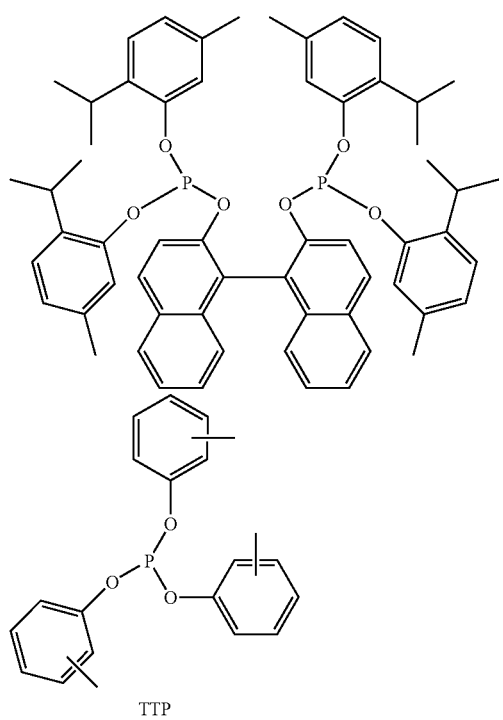

After flashing the PNs, the reaction medium obtained has the following composition (% expressed by weight; the ratios are molar ratios):
Ni=0.58%
TTP/Ni=5
Ligand A/Ni=1.2
P/Ni=7.4
DN=64.0%
PN=6.4%
$ZnCl_2$=0.16%

The mixture is cooled to 50° C.: separation into two liquid phases is observed. The dense phase comprises approximately 83% of the Ni(0) and approximately 73% of the ligand A. The TTP/Ni ratio is approximately 3 in the lower phase and approximately 15 in the upper phase. The TTP/ligand A molar ratio is close to 8 in the upper phase.

The upper phase, which comprises adiponitrile, is subjected to a liquid/liquid extraction with cyclohexane. The cyclohexane solution obtained is evaporated. The recovery of the catalytic system as residue from the evaporation is quantitative.

EXAMPLE 2

Settling of the TTP/ligand B Mixed System

Example 1 is repeated but replacing the ligand A by the ligand B with the following formula:

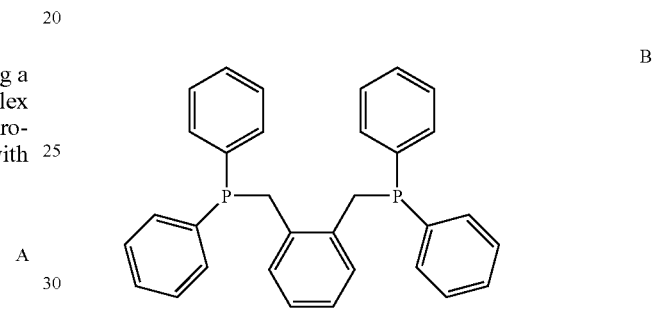

After flashing the PNs, the reaction medium obtained has the following composition (% expressed by weight; the ratios are molar ratios):
Ni=0.70%
TTP/Ni=4
Ligand B/Ni=1
P/Ni=6
DN=67.7%
PN=6.7%
$ZnCl_2$=0.17%

The medium is cooled to 50° C.: separation into two liquid phases is observed. The dense phase comprises approximately 70% of the Ni(0) and approximately 70% of the ligand B. The TTP/Ni ratio is less than 2 in the dense phase and approximately equal to 9 in the light phase. The TTP/ligand B ratio is close to 9 in the light phase.

The upper phase is subjected to a liquid/liquid extraction with cyclohexane. The cyclohexane solution is evaporated. The recovery of the catalytic system as residue from the evaporation is quantitative.

The invention claimed is:
1. A process for the preparation of dinitrile compounds by hydrocyanation of unsaturated mononitrile compounds in a reaction medium and in the presence of a catalytic system comprising an organometallic complex formed from zerovalent nickel and from a mixture of organophosphorus ligands comprising at least one monodentate organophosphite compound and at least one bidentate organophosphorus compound selected from the group consisting of organophosphites, organophosphinites, organophosphonites and organophosphines, and optionally a promoter, said process comprising a recovery of the catalytic system, and comprising the steps of:

a) controlling the concentration of unsaturated nitriles in the reaction medium resulting from the hydrocyanation reaction in order to obtain a concentration by weight of unsaturated nitriles of less than 20% in said medium,
b) feeding the said medium to a stage of settling into two upper and lower phases,
c) separating the two phases, the lower phase comprising most of the nickel and of the bidentate ligand, and a portion of the monodentate ligand,
d) at least partially recycling said lower phase to a hydrocyanation stage, and
e) subjecting the upper phase to a liquid/liquid extraction in order to extract the organometallic complex and the organophosphorus compounds present in said upper phase.

2. The process according to claim 1, wherein the reaction medium is cooled to a temperature of between 25° C. and 75° C. before being introduced into the settling stage, and wherein said lower phase comprises no more than 50% of the monodentate ligand.

3. The process according to claim 1, wherein nickel in the medium fed to the settling stage has a concentration by weight of between 0.2 and 2%, and wherein the unsaturated nitriles have a concentration by weight in the medium fed to the settling stage of between 4% and 20% by weight.

4. The process according to claim 3, wherein the concentration of unsaturated nitrites in the reaction medium resulting from the hydrocyanation stage is less than 20% by weight.

5. The process according to claim 1, wherein the reaction medium resulting from the hydrocyanation stage is fed to a stage of distillation of the unsaturated nitrites, the distillation bottoms being fed to the settling stage.

6. The process according to claim 1, wherein the lower phase from the settling stage is at least partially recycled in the reaction medium resulting from the hydrocyanation.

7. The process according to claim 6, wherein a portion of the said lower phase is recycled in the reaction medium resulting from the hydrocyanation, before the stage of distillation of the unsaturated nitrites.

8. The process according to claim 1, wherein the bidentate ligand has a number of moles, expressed as number of phosphorus atoms with respect to a metal element atom, of between 1 and 4 in the hydrocyanation medium.

9. The process according to claim 1, wherein the monodentate ligand has a number of moles, expressed as number of phosphorus atoms with respect to a metal element atom, in the hydrocyanation medium of between 4 and 7.

10. The process according to claim 1, wherein the solvent used for carrying out the liquid/liquid extraction of the catalyst and of the organophosphorus compounds present in the upper phase is a saturated or unsaturated, aliphatic or cycloaliphatic hydrocarbon.

11. The process according to claim 1, wherein the catalyst and the organophosphorus ligands extracted in the liquid/liquid extraction stage are recovered by evaporation of the extraction solvent.

12. The process according to claim 10, wherein the extraction solvent is hexane, heptane, octane, cyclohexane, cyclopentane or cycloheptane.

13. The process according to claim 1, wherein the organophosphorus ligands have a number of moles, expressed as number of phosphorus atoms, in the medium fed to the liquid/liquid extraction stage with respect to a metal element atom, of greater than 8.

14. The process according to claim 1, wherein the monodentate ligand is a triphenyl phosphite, tritolyl phosphite or tricymenyl phosphite.

15. The process according to claim 1, wherein the bidentate organophosphorus ligand is an organophosphite, organophosphonite, organophosphinite or organophosphine.

16. The process according to claim 15, wherein the bidentate organophosphorus ligand is one of the compounds with the following structures, wherein Ph means phenyl:

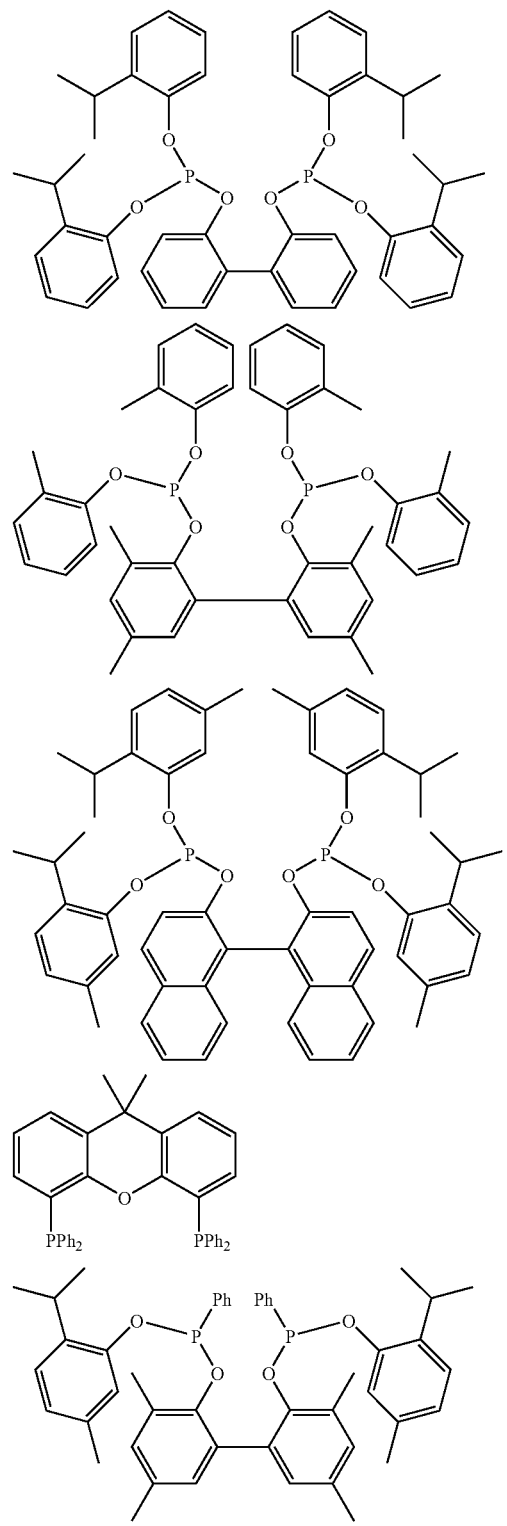

-continued

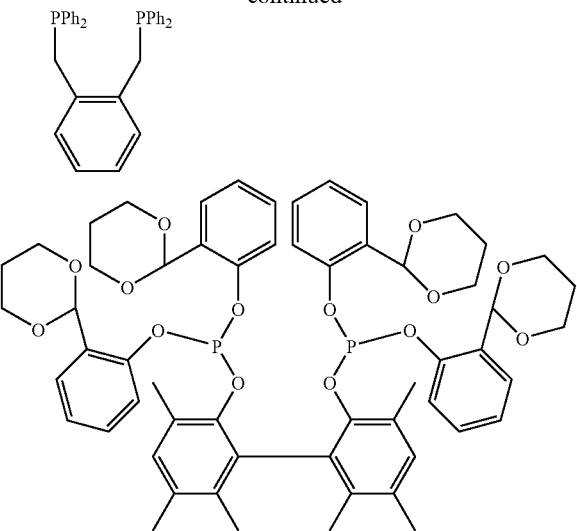

17. The process according to claim 1, wherein the catalytic system further comprises a promoter or cocatalyst composed of a Lewis acid.

18. The process according to claim 17, wherein the promoter is selected from the group consisting of halides, sulphates, sulphonates, haloalkylsulphonates, perhaloalkylsulphonates, haloacetates, perhaloacetates, carboxylates, phosphates, arylboranes, fluoroalkylsuiphonates and perfluoroalkylsulphonates of elements from Groups Ib, IIb, IIIa, IIIb, IVa, IVb, Va, Vb, VIb, VIIb or VIII of the Periodic Table of the Elements.

19. The process according to claim 18, wherein the Lewis acid is selected from the group consisting of zinc chloride, zinc bromide, zinc iodide, manganese chloride, manganese bromide, cadmium chloride, cadmium bromide, stannous chloride, stannous bromide, stannous sulphate, stannous tartrate, indium chloride, indium trifluoromethylsulphonate, indium trifluoro-acetate, the chlorides of rare earth elements, the bromides of rare earth elements, cobalt chloride, ferrous chloride, yttrium chloride, triphenylborane, and titanium tetraisopropoxide.

20. The process according to claim 6, wherein the column bottom temperature in the stage of distillation of the unsaturated nitriles is less than 140° C.

21. The process according to claim 1, wherein the unsaturated nitrile is a linear or branched aliphatic compound comprising from 3 to 8 carbon atoms.

22. The process according to claim 1, wherein the catalytic system solution recovered after the stage of liquid/liquid extraction is subjected to distillation of the extraction solvent, the bottom temperature of this distillation being less than 180° C.

23. The process for the manufacture of dinitrile compounds from diolefins, comprising a first stage of hydrocyanation of the diolefin to give unsaturated mononitriles, optionally an isomerization reaction of the branched unsaturated mononitriles formed in the first stage, and a second stage of hydrocyanation of the unsaturated mononitriles to give dinitrile compounds as defined in claim 1.

24. The process according to claim 23, wherein the catalyst recovered from the upper phase of the settling stage is at least partially recycled in the isomerization reaction and/or to the first hydrocyanation stage.

25. The process according to claim 24, wherein the catalyst recovered from the upper phase of the settling stage is at least partially recycled in the isomerization reaction and then in the first hydrocyanation stage.

26. The process according to claim 25, wherein the catalyst recovered from the hydrocyanation medium of the first stage is fed to the settling stage or to the liquid/liquid extraction stage.

* * * * *